(12) United States Patent
Corey

(10) Patent No.: US 6,815,544 B2
(45) Date of Patent: Nov. 9, 2004

(54) SYNTHETIC PROCESS FOR AN INTERMEDIATE FOR ECTEINASCIDIN AND PHTHALASCIDIN COMPOUNDS

(75) Inventor: Elias J. Corey, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 38 days.

(21) Appl. No.: 10/213,711

(22) Filed: Aug. 7, 2002

(65) Prior Publication Data
US 2003/0083495 A1 May 1, 2003

Related U.S. Application Data

(63) Continuation of application No. PCT/US01/04376, filed on Feb. 9, 2001.
(60) Provisional application No. 60/181,795, filed on Feb. 11, 2000.

(51) Int. Cl.[7] ............................................. C07D 498/18
(52) U.S. Cl. ........................................ 544/99; 544/338
(58) Field of Search .................................. 544/99, 338

(56) References Cited

U.S. PATENT DOCUMENTS

| 5,721,362 A | 2/1998 | Corey et al. ................. 540/466 |
| 6,124,292 A | 9/2000 | Corey ......................... 514/250 |

OTHER PUBLICATIONS

Cuevas, et al. Synthesis of Ecteinascidin ET–743 and Phthalascidin Pt–650 from Cyanosafracin B. Organic Letters. (Jul. 19, 2000), vol. 2, No. 16, pp. 2545–2548.
Martinez, et al. A New, More Efficient, and Effective Process For the Synthesis of a Key Pentacyclic Intermediate for Production of Ecteinascidin and Phthalascidin Antitumor Agents. Organic Letters. (Mar. 15, 2000), vol. 2, No. 7, pp. 993–996.
Corey, et al. Enantioselective Total Synthesis of Ecteinascidin 743. J. Am. Chem. Soc. 1996, 118, 9202–3.
Greene, et al. Protective Groups in Organic Synthesis. New York: John Wiley & Sons, Inc. 1991, second edition, pp. 77 and 83.

Primary Examiner—Bruck Kifle

(57) ABSTRACT

An efficient process is described for the synthesis of 5, a key intermediate for the synthesis of the potent antitumor agents ecteinascidin 743 (1) and phthalascidin (2) from the readily available building blocks 3b and 4.

15 Claims, No Drawings

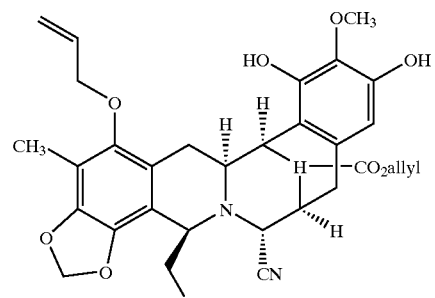

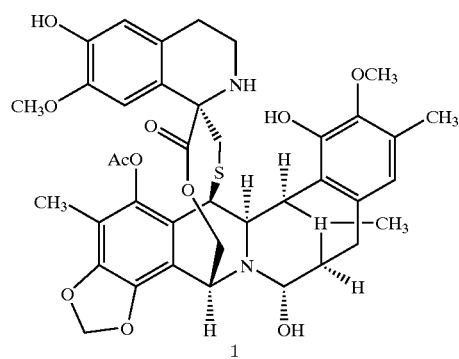

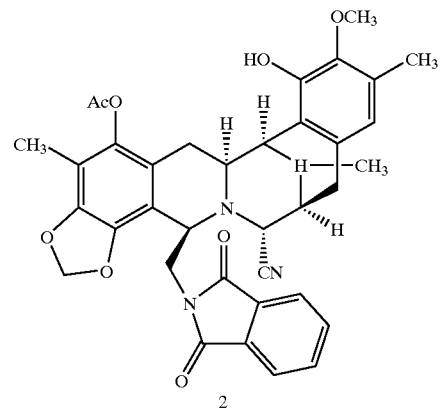

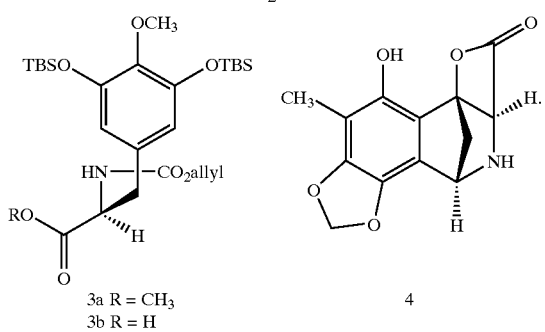

SYNTHETIC PROCESS FOR AN INTERMEDIATE FOR ECTEINASCIDIN AND PHTHALASCIDIN COMPOUNDS

PRIORITY CLAIM AND CROSS-REFERENCE TO RELATED APPLICATIONS

This application is a continuation of PCT Application No. PCT/US01/04376 filed Feb. 9, 2001, which was published in English on Aug. 16, 2001 as WO 01/58905. The PCT Application claims priority from U.S. Provisional Application Ser. No. 60/181,795, filed 11 Feb. 2000. The disclosures of these applications are hereby incorporated herein by reference.

STATEMENT OF GOVERNMENT SUPPORT

This invention was supported by funding from the Government of the United States of America, by virtue of Grant No. GM34167 awarded by the National Institutes of Health. Thus, the Governmant may have certain rights in this invention.

BACKGROUND OF THE INVENTION

Ecteinascidin 743 (1, Et 743) is an exceedingly potent marine-derived antitumor agent[1] which is now being studied in various clinics with human patients.[2] Because this compound is not sufficiently available from the natural source, the tunicate *Ecteinascidia turbinata*, it is being produced industrially by the totally synthetic route described in 1996.[3] More recently a structural analog of Et 743, compound 2 (phthalascidin, Pt 650) has been found to exhibit antitumor activity essentially indistinguishable from 1.[4]

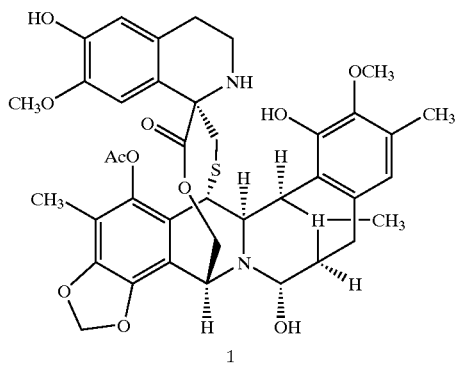

1

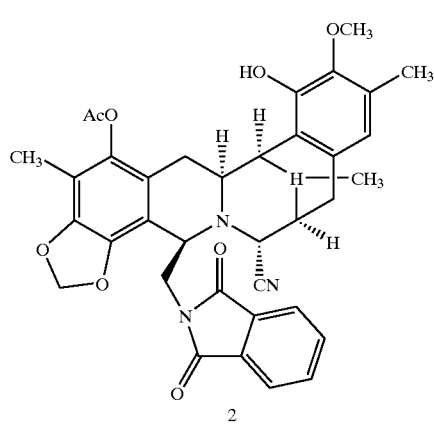

2

Both 1 and 2 are synthesized from building blocks 3 and 4[3] via a common pentacyclic intermediate 5.

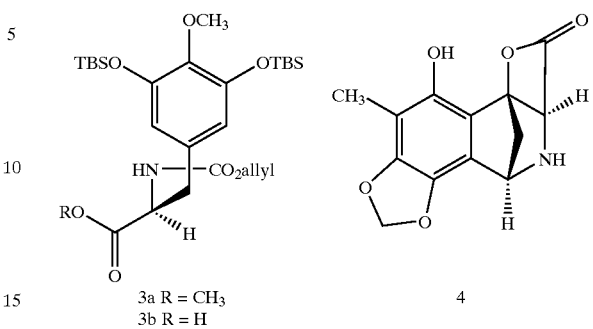

3a R = CH₃
3b R = H

4

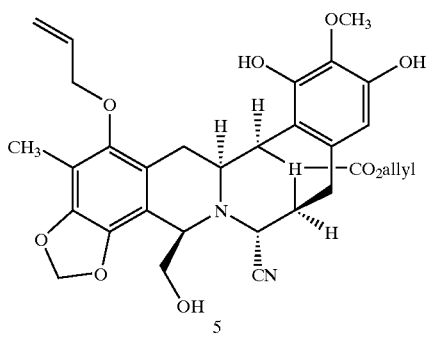

5

The synthesis of 5 was accomplished originally[3] from building blocks 3a and 4 in six steps with an overall yield of 35% (average yield per step of ca. 84%). Because the industrial syntheses of 1 and/or 2 would eventually have to be produced economically on a multi-kilogram scale, we sought to find a more efficient and reproducible alternative route from 2 and 3 to 5.

SUMMARY OF THE INVENTION

One embodiment of the present invention is thus directed to a new synthetic process for the preparation of the intermediate compound 5 which is simpler to carry out than the original and which proceeds from 3b[3]+4 to 5 in six steps with an overall yield of 57% (average yield per step of nearly 92%). The preferred process for the synthesis of pentacycle 5 is summarized below in Scheme 1.[5]

Scheme 1
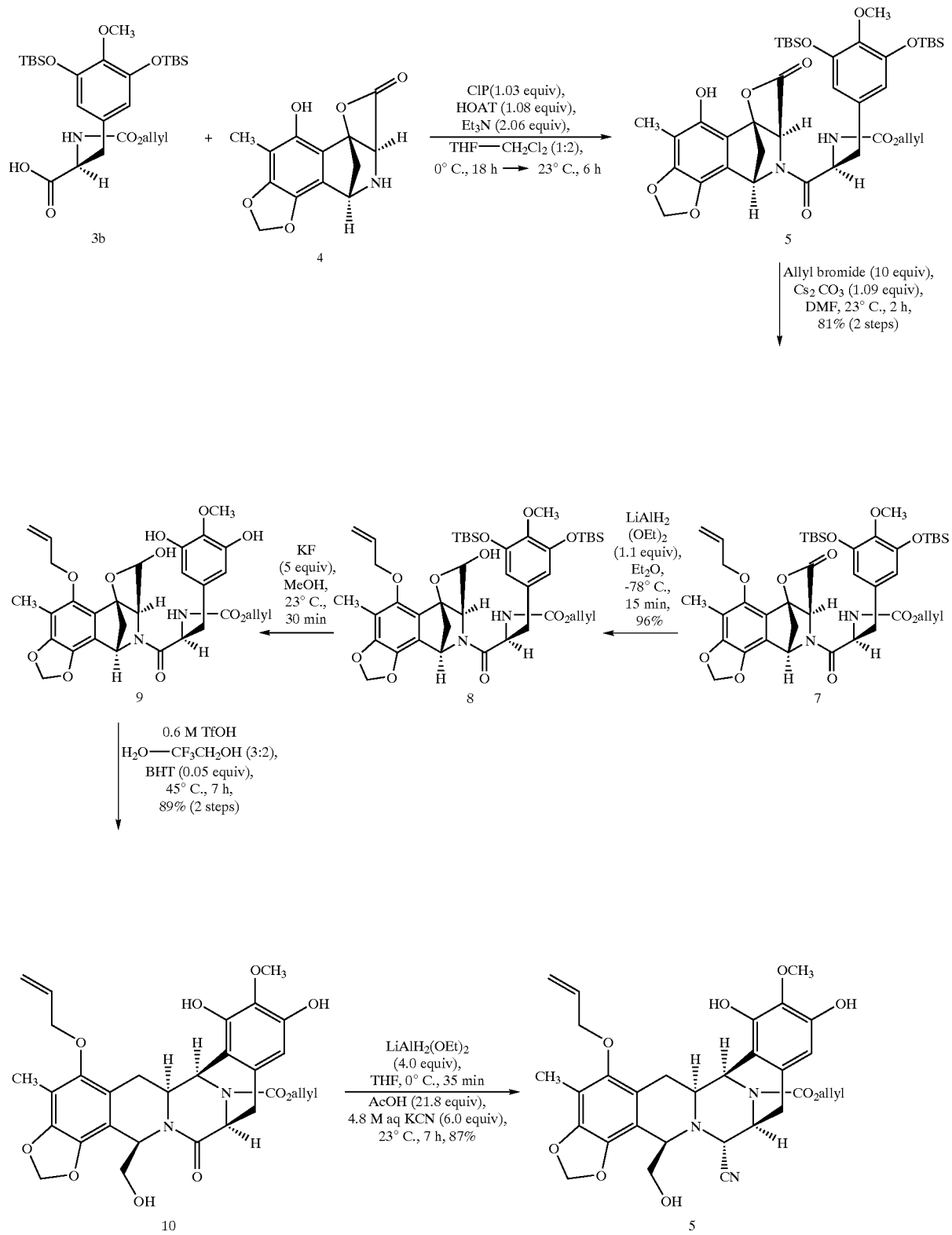

The second preferred embodiment of the present invention entails a new synthetic process for converting the pentacycle compound 5 to phthalascidin 2, which proceeds smoothly and in excellent yield (average yield per step 90.8%). This process is outlined below in Scheme 2.

from the acid 3b[3] (1.03 equiv), 1-hydroxy-7-azabenzotriazole (HOAT, 1.08 equiv), 2-chloro-1,3-dimethylimidazolidinium hexafluorophosphate (CIP, 1.03 equiv) and triethylamine (2.06 equiv) in $CH_2Cl_2$ solution at 0 EC.[6]

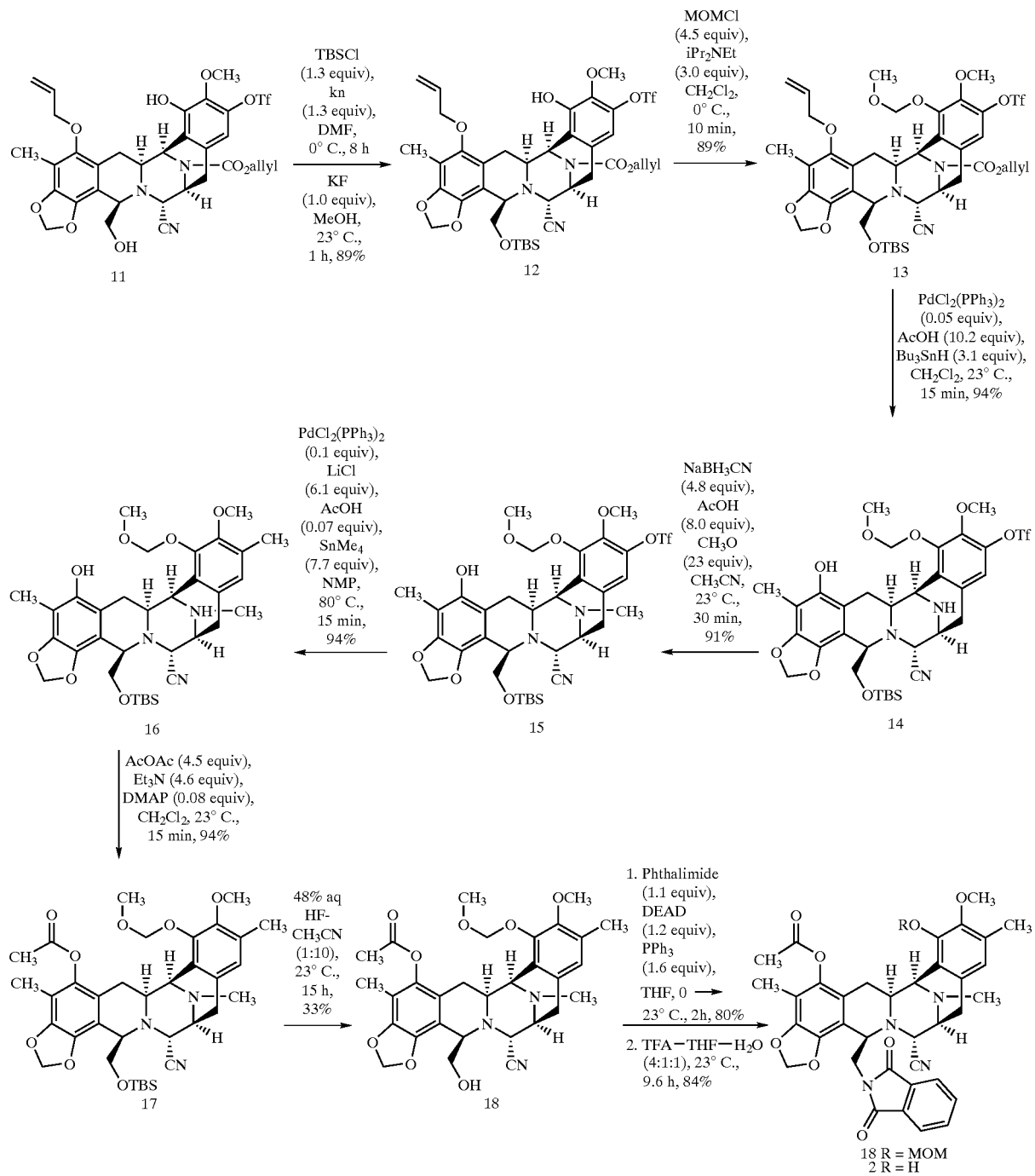

Scheme 2

DETAILED DESCRIPTION OF THE PREFERRED EMBODIMENTS

As illustrated above in Scheme 1, a solution of azeotropically dried ($C_7H_8$BTHF) amino lactone 4 in THF at 0 EC was treated dropwise with an acylating reagent prepared The coupling product 6, which was obtained by extractive workup, was allylated without further purification by treatment in DMF solution at 23 EC with excess allyl bromide and 1.09 equiv of $Cs_2CO_3$ to give amide 7 in 81% overall yield from 3a and 4 after flash chromatography on silica gel.

Selective reduction of the lactone function of 7 to the corresponding lactol (8) was effected by reaction with 1.1 equiv of lithium diethoxyaluminum hydride (LiAlH$_2$(OEt)$_2$) in ether at −78E for 15 min in 95% yield.[7,8] Desilylation of 8 to 9 and cyclization of 9 (without purification) using 0.6 M triflic acid in 3:2H$_2$O$\text{B}$CF$_3$CH$_2$OH at 45 EC for 7 h produced the pentacyclic product 10 in 89% overall yield from 8.

Finally, the lactam function of 10 could be reduced cleanly by treatment with 4 equiv of LiAlH$_2$(OEt)$_2$ in THF at 0 EC for 35 min to the corresponding cyclic aminal which upon exposure to HCN provided the pentacyclic amino nitrile 5 in 87% overall yield from 10 after flash chromatography on silica gel.[9]

The synthesis of 5 which is outlined in Scheme 1 and described above is advantageous relative to the originally used synthetic pathway[3] not only because of the substantially greater overall yield (57 vs 35%), but also because of the simplicity and reproducibility of the individual steps, especially the amide coupling (2a+3→6) and the internal Pictet-Spengler cyclization (9→10). In addition no difficulties have been encountered either in product purification or scale up.

A critical element to the success of the sequence shown in Scheme 1 was the high efficiency and selectivity of LiAlH$_2$(OEt)$_2$ for the two reduction steps: 8→9 and 10→5, which suggest that this reagent can be used to advantage in synthesis much more frequently than it has been previously.

In Scheme 2, the pentacyclic triol 5 was first converted to the phenolic monotriflate 11 (step not shown) by treatment with 1.1 equiv of PhNTf$_2$ (McMurry reagent), 2 equiv of Et$_3$N and 0.2 equiv of 4-dimethyl-aminopyridine in CH$_2$Cl$_2$ at −30 EC for 38 h (74%). Conversion of 11 to the mono t-butyldimethylsilyl (TBS) ether 12 and etherification with methoxymethyl chloride (MOMCl) produced 23 in high yield.

Cleavage of the N-allyloxycarbonyl and O-allyl groups in 13 gave the secondary amine 14 (94%) which was N-methylated to 15 and C-methylated to 16. Acetylation of phenol 16 produced the corresponding acetate 17 which upon desilylation formed the primary alcohol 18. Mitsunobu displacement of the primary hydroxyl of 18 produced the phthalimide 19 which upon acid-catalyzed cleavage of the methoxymethyl ether provided pure phthalascidin 2.

Since the original synthetic route to Et 743 (1) has proved to be acceptable for large scale synthesis, it is our expectation that the improved process described herein will be even more useful, as will the new route to phthalascidin (2).[4] Because phthalascidin is more stable than ecteinascidin 743 and considerably easier to make, it may prove to be a more practical therapeutic agent.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

Example 1

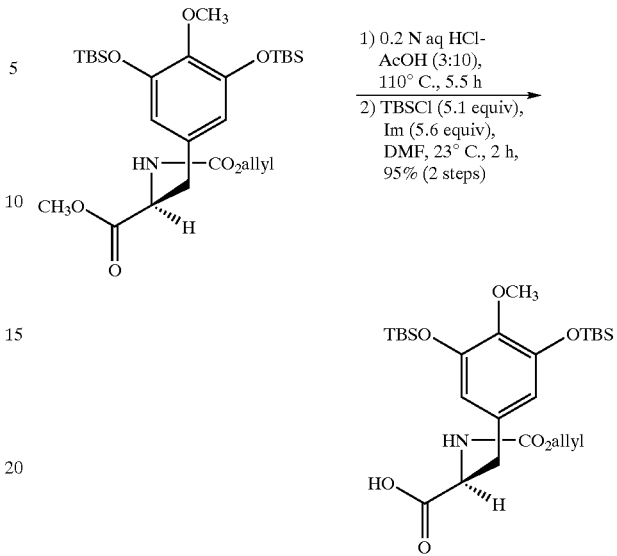

The acid (224 mg, 0.400 mmol) was dissolved in distilled acetic acid (5.0 mL) and 0.2 N HCl[10] (1.5 mL) and heated to 110 EC. After 5.5 h, the reaction was concentrated in vacuo and dried by repetitive in vacuo azeotropic concentration with toluene (3×10 mL) and dissolved in DMF (1.0 mL). tert-Butyldimethylsilyl chloride (304 mg, 2.03 mmol) and imidazole (152 mg, 2.24 mmol) were added as solids and the mixture was stirred at 23 EC for 2 h. The reaction was quenched with 2:1 acetic acid-water (1.5 mL) and stirred for 30 min. The reaction was poured into 0.5 M aqueous oxalic acid (100 mL) and extracted with 3:7 ethyl acetate-hexane (2×100 mL). The combined organic layers were washed with saturated aqueous sodium chloride (100 mL), dried over sodium sulfate, filtered and concentrated in vacuo. The residue was purified by flash column chromatography (100 mL silica gel, gradient 1:1 ethyl acetate-hexane to 0.1% acetic acid-ethyl acetate) to afford the desired product as a substantially pure clear viscous oil (204.6 mg, 95%).

$R_f$ 0.10 (ethyl acetate); $^1$H NMR (400 MHz, CDCl$_3$) δ 10.25 (br s, 1H), 6.32 (s, 2H), 5.90 (ddt, J=17.0, 10.6, 5.4 Hz, 1H), 5.28 (d, J=17.1 Hz, 1H), 5.20 (d, J=10.4 Hz, 1H), 5.11 (d, J=8.0 Hz, 1H), 4.61–4.57 (m, 1H), 4.55 (d, J=5.5 2H), 3.70 (s, 3H), 3.04 (dd, J=14.0, 5.1 Hz, 1H), 2.93 (dd, J=14.0, 6.4 Hz, 1H), 0.99 (s, 18H), 0.15 (s, 12H); $^{13}$C NMR (101 MHz, CDCl$_3$) δ 176.3, 155.7, 149.9, 142.2, 132.5, 130.5, 118.0, 115.6, 66.1, 60.0, 54.5, 37.2, 25.8, 18.4, −4.6; FTIR (neat) 3438 (m), 3331 (m), 3088 (m v br), 2956 (s), 2931 (s), 2894 (s), 2863 (s), 1719 (s), 1578 (s), 1496 (s), 1435 (s), 1361 (s), 1253 (s), 1231 (s), 1093 (s), 1010 (m), 938 (w), 831 (s) cm$^{-1}$; HPLC analysis was performed after derivatization using diazomethane to make the methyl ester (ChiralPak AD, 1% isopropanol in hexane, flow rate: 1.0 mL/min, λ=226 nm), 96% ee, $R_T$=11.1 min (major), 9.2 min (minor); HRMS (FAB), [m+H]/z calc=d for C$_{26}$H$_{46}$O$_7$NSi$_2$: 540.2813, found 540.2823; $[\alpha]_D^{23}$+18.8E (c 1.0, methylene chloride).

Example 2

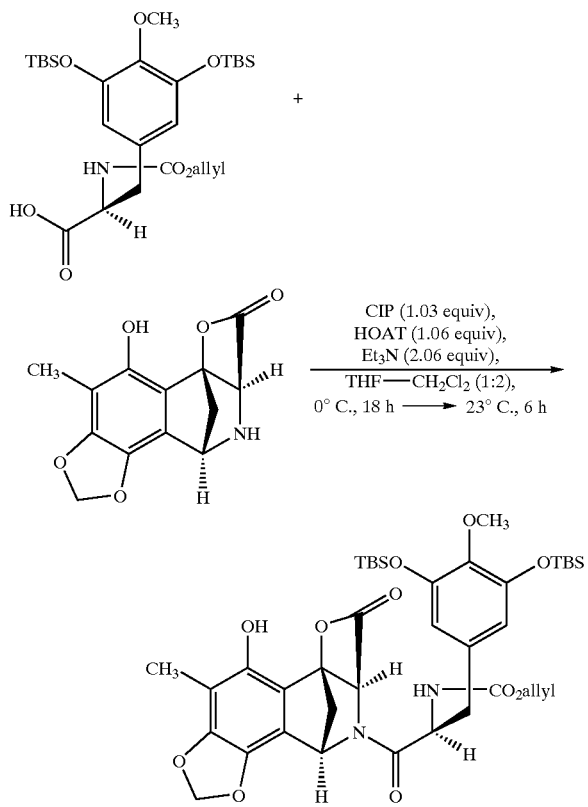

The amine (100.0 mg, 0.380 mmol) was dried by in vacuo azeotropic concentration with 2:3 THF-toluene (5 mL) and dissolved in THF (1.5 mL) and cooled to 0 EC. In a different flask, the acid (211.7 mg, 0.392 mmol) and 1-hydroxy-7-azabenzotriazole (55.8 mg, 0.410 mmol) were dried by in vacuo azeotropic concentration with 2:3 THF-toluene (5 mL) and dissolved in methylene chloride (1.5 mL). To this flask was added 2-chloro-1,3-dimethylimidazolidinium hexafluorophosphate (109.3 mg, 0.392 mmol) as a solid and triethylamine (109 μL, 0.782 mmol) via syringe to afford a clear dark yellow solution. This mixture was stirred at 23 EC for 3 min and then cooled to 0 EC and cannulated into the flask containing the amine. Methylene chloride (1.5 mL) was used to transfer the remains in the flask. The golden solution was stirred at 0 EC for 18 h, warmed to 23 EC and stirred an additional 6 h. The reaction was diluted with ethyl acetate (6 mL) and partially concentrated in vacuo to remove methylene chloride. The solution was poured into 0.5 M aqueous acetic acid (100 mL), extracted with 3:7 ethyl acetate-hexane (100 mL) and washed with saturated aqueous sodium bicarbonate (100 mL). The aqueous layers were re-extracted 3:7 ethyl acetate-hexane (100 mL) and the combined organic layers were dried over sodium sulfate, filtered and concentrated in vacuo to afford a clear film (~300 mg). This residue was used without further purification. The material can be purified by flash column chromatography (100 mL silica gel, gradient 1:3 to 2:3 ethyl acetate-hexane), however only a 50% yield was obtained presumably due to silica gel promoted decomposition.

$R_f$ 0.36 (2:3 ethyl acetate-hexane); $^1$H NMR (400 MHz, CDCl$_3$) δ (mixture of carbamate and amide rotamers) 6.35 (s, 1H), 6.20 (s, 1H), 5.91–5.81 (m, 3H), 5.94–5.59 (m, 1.5H), 5.42 (d, J=3.3 Hz, 0.5H), 5.30–5.03 (m, 3H), 4.74–4.63 (m, 1H), 4.60 (dd, J=10.8, 3.1 Hz, 0.5H), 4.53 (br s, 1H), 4.45 (d, J=5.1 Hz, 1H), 4.36 (d, J=10.6 Hz, 0.5H), 4.19 (d, J=10.6 Hz, 0.5H), 3.68 (s, 1.5H), 3.61 (s, 1.5H), 3.56 (d, J=8.4 Hz, 0.5H), 3.03–2.90 (m, 3H), 2.79 (dd, J=13.0, 4.6 Hz, 0.5H), 2.24 (d, J=16.0 Hz, 0.5H), 2.06 (br s, 3H), 0.99 (s, 9H), 0.91 (s, 9H), 0.15 (s, 6H), 0.06 (s, 6H); 13C NMR (101 MHz, CDCl$_3$) δ (mixture of carbamate and amide rotamers) 169.2, 169.0, 167.9, 167.5, 155.6, 155.2, 150.1, 149.7, 146.9, 146.5, 145.1, 145.0, 142.1, 141.7, 136.8, 136.2, 132.4, 132.3, 130.7, 130.3, 117.9, 117.8, 115.5, 115.3, 111.3, 110.9, 110.5, 108.1, 107.8, 101.4, 73.0, 66.1, 65.9, 60.0, 59.9, 54.7, 52.2, 51.9, 51.0, 47.6, 43.2, 39.6, 38.5, 29.1, 27.4, 25.8, 25.7, 18.4, 18.3, 8.9, −4.53, −4.56, −4.65, −4.74; FTIR (neat) 3406 (w br), 3319 (w br), 2956 (m), 2931 (m), 2894 (w), 2856 (m), 1725 (m), 1644 (m), 1575 (m), 1494 (m), 1463 (m), 1431 (s), 1356(w), 1231 (s), 1163 (w), 1094(s), 1044 (m), 1013 (m), 831 (s) cm$^{-1}$; HRMS (ESI), [m+H]/z calc=d for C$_{39}$H$_{57}$O$_{11}$N$_2$Si$_2$: 785.3501, found 785.3469; $[\alpha]_D^{24}$+20.5E (c 1.0, chloroform).

Example 3

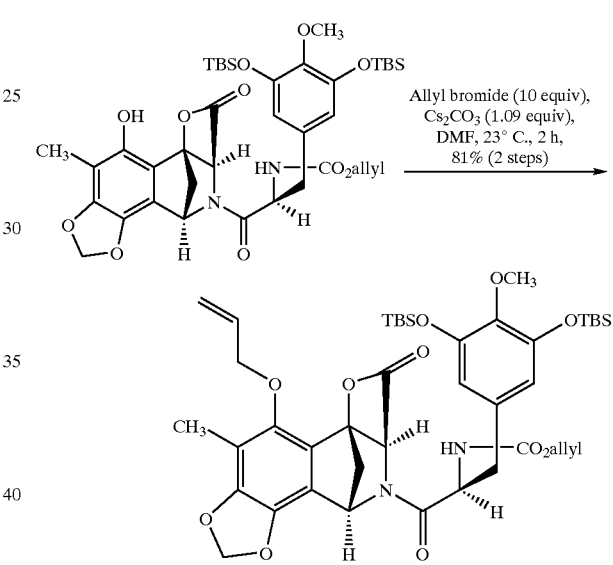

Phenol (~300 mg, 0.380 mmol) was dried by in vacuo azeotropic concentration with toluene (5 mL) and dissolved in DMF (15 mL). Allyl bromide (330 μL, 3.82 mmol) was added via syringe and cesium carbonate (134.7 mg, 0.413 mmol), gently flame dried in vacuo, was added as a solid and the reaction was stirred at 23 EC for 2 h. The reaction was poured into water (300 mL), extracted with 1:4 ethyl acetate-hexane (2×150 mL), washed with saturated aqueous sodium chloride (100 mL), dried over sodium sulfate, filtered and concentrated in vacuo. The residue was purified by flash column chromatography (75 mL silica gel, gradient 1:4 to 3:7 ethyl acetate-hexane) to afford the desired product as a substantially pure clear film (252.9 mg, 81% over two steps). This material was also found to be unstable to silica gel and so a rapid chromatography was critical to obtain the observed yield.

$R_f$ 0.47 (2:3 ethyl acetate-hexane); $^1$H NMR (400 MHz, CDCl$_3$) δ (mixture of carbamate and amide rotamers) 6.35 (s, 1H), 6.20 (s, 1H), 6.03–5.78 (m, 5H), 5.52–5.44 (m, 1.4H), 5.38–5.33 (m, 1H), 5.31–5.13 (m, 3.6H), 4.73–4.59 (m, 1.4H), 4.55 (d, J=5.1 Hz, 1H), 4.48 (d, J=5.1 Hz, 1H), 4.34 (d, J=10.6 Hz, 0.6H), 4.24–4.04 (m, 3H), 3.68 (s, 1.5H), 3.60 (s, 1.5H), 3.54 (d, J=8.8 Hz, 0.4H), 2.90 (m, 2.6H), 2.77

(dd, J=12.8, 4.8 Hz, 0.6H), 2.34 (m, 0.4H), 2.12 (s, 1.5H), 2.09 (s, 1.5H), 0.99 (s, 9H), 0.92 (s, 9H), 0.16 (s, 6H), 0.07 (s, 3H), 0.05 (s, 3H); $^{13}$C NMR (101 MHz, CDCl$_3$) δ (mixture of carbamate and amide rotamers) 169.2, 168.8, 167.4, 167.1, 155.5, 155.1, 150.2, 150.0, 149.8, 145.5, 145.3, 142.2, 141.9, 139.2, 138.8, 133.4, 133.2, 132.4, 130.6, 130.2, 118.3, 118.0, 117.9, 117.8, 117.7, 117.2, 115.5, 115.2, 114.3, 113.9, 111.1, 110.9, 101.8, 101.7, 73.8, 73.7, 72.8, 66.1, 65.9, 60.04, 59.99, 54.9, 52.1, 51.9, 51.1, 47.7, 43.3, 39.8, 38.5, 29.6, 27.9, 25.8, 25.7, 18.4, 18.3, 9.6, 9.4, −4.51, −4.54, −4.6, −4.7; FTIR (neat) 3306 (w br), 2956 (m), 2931 (m), 2898 (m), 2856 (m), 1750 (m), 1719 (m), 1650 (m), 1575 (m), 1494 (m), 1431 (s), 1363 (m), 1250 (m), 1231 (m), 1163 (w), 1094 (s), 1044 (m), 1013 (m), 944 (w), 919 (w), 831 (s) cm$^{-1}$; HRMS (ESI), [m+H]/z calc=d for C$_{42}$H$_{61}$O$_{11}$N$_2$Si$_2$: 825.3814, found 825.3788; [α]$_D^{24}$+21.7E (c 1.0, chloroform).

Example 4

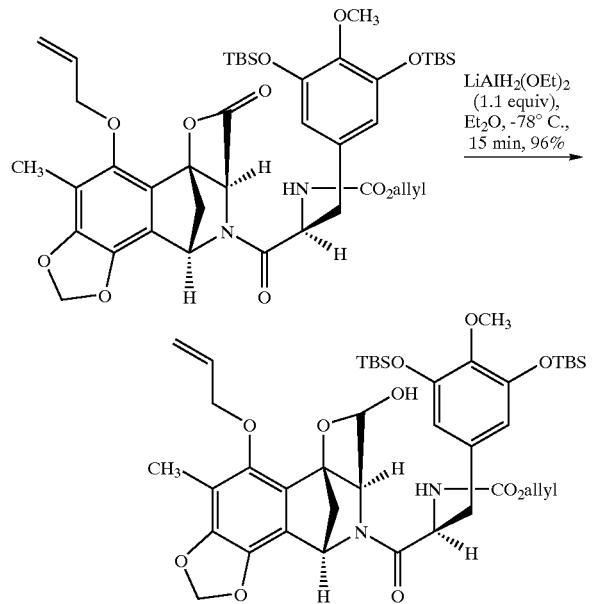

The lactone (354.1 mg, 0.429 mmol) was dried by in vacuo azeotropic concentration with toluene (10 mL), dissolved in diethyl ether (8.0 mL) and cooled to −78 EC in a dry ice-acetone bath. A 0.10 M solution of LiAlH$_2$(OEt)$_2$ (4.7 mL, 0.47 mmol)[11] was added drop-wise down the side of the flask over 2 min. The reaction was stirred at −78 EC for 15 min and then the light yellow solution was poured in 0.1 N HCl (50 mL) at 0 EC while rapidly stirring. This solution was extracted with diethyl ether (2×75 mL), washed with saturated aqueous sodium chloride (50 mL), dried over sodium sulfate, filtered and concentrated in vacuo. The residue was purified by flash column chromatography (150 mL silica gel, gradient 3:7 to 2:3 to 1:1 ethyl acetate-hexane) to afford the desired product as a substantially pure clear film (339.0 mg, 95%).

R$_f$ 0.20 (2:3 ethyl acetate-hexane); $^1$H NMR (400 MHz, CDCl$_3$) δ (mixture of anomers, carbamate and amide rotamers) 6.43 (s, 0.2H), 6.37 (s, 0.2H), 6.16 (s, 1.4H), 6.15 (s, 0.2H), 6.05–5.80 (m, 4.4H), 5.82–5.59 (m, 1.2H), 5.41–5.14 (m 3.8H), 5.07–4.95 (m, 1.5H), 4.85–4.76 (m, 1.6H), 4.61–4.46 (m, 2.2H), 4.26-4.41 (m, 3.8H), 4.10–3.75 (m, 0.5H), 3.68 (s, 0.3H), 3.66 (s, 0.3H), 3.63 (s, 2.4H), 3.37 (d, J=11.0 Hz, 0.8H), 3.33–2.94 (m, 0.7H), 2.90–2.65 (m, 2.8H), 2.35 (dd, J=17.7 7.5 Hz, 0.7H), 2.12 (s, 0.3H), 2.11 (s, 0.3H), 2.09 (s, 2.4H), 1.05 (s, 4.5H), 0.92 (s, 13.5H), 0.16 (s, 4.5H), 0.07 (s, 4.5H), 0.04 (s, 4.5H); $^{13}$C NMR (101 MHz, CDCl$_3$) δ (mixture of anomers, carbamate and amide rotamers) 169.8, 156.1, 149.6, 149.2, 144.6, 141.7, 138.3, 133.8, 132.2, 130.2, 118.9, 118.0, 116.7, 115.1, 113.4, 112.5, 101.3, 93.4, 73.2, 66.2, 62.4, 60.1, 53.6, 51.4, 44.6, 38.5, 26.5, 25.9, 25.8, 18.5, 18.3, 9.5, −4.56, −4.59; FTIR (neat) 3406 (m br), 3325 (m br), 2956 (m), 2931 (m), 2894 (m), 2856 (m), 1714 (m), 1644 (m), 1578 (m), 1496 (m), 1433 (s), 1360 (m), 1255 (m), 1234 (m), 1095 (s), 1044 (m), 1013 (m), 941 (w), 830 (s) cm$^{-1}$; HRMS (ESI), [m+H]/z calc=d for C$_{42}$H$_{63}$O$_{11}$N$_2$Si$_2$: 827.3970, found 827.4009; [α]$_D^{25}$−1.5E (c 1.0, chloroform).

Example 5

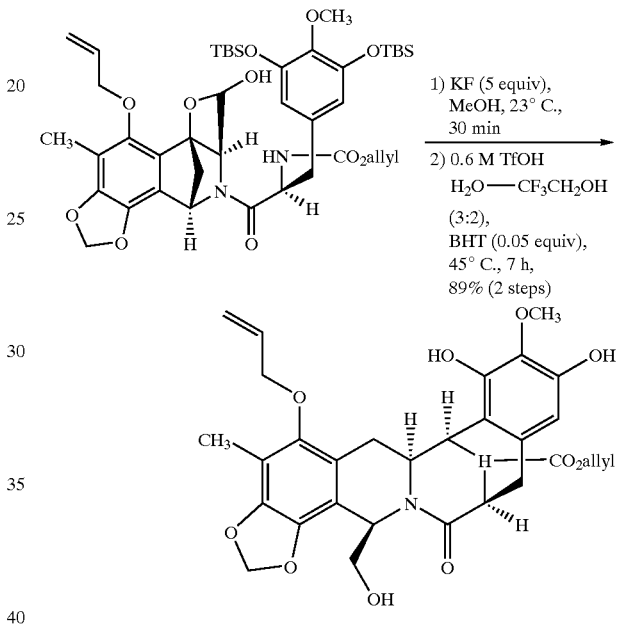

The lactol (316.3 mg, 0.382 mmol) was dissolved in nitrogen purged methanol (3.8 mL). Anhydrous potassium fluoride (110.3 mg, 1.90 mmol) was added as a solid and the vessel was pumped/purged with nitrogen. The reaction was stirred at 23 EC for 30 min and the light pink mixture was diluted with toluene (5 mL) and concentrated in vacuo. The residue was dissolved in nitrogen purged 2,2,2-trifluoroethanol (15 mL) and butylated hydroxytoluene (4.3 mg, 0.02 mmol) was added as a solid. The flask was charged with 1.0 M aqueous trifluoromethanesulfonic acid[12] (23 mL) and the vessel was again pumped/purged with nitrogen. The solution was stirred at 45 EC in an oil bath for 7 h. The mixture was partially concentrated in vacuo, to remove the alcohol, and poured into 80% saturated aqueous sodium chloride (100 mL), extracted with ethyl acetate (2×100 mL), washed with saturated aqueous sodium chloride (50 mL), dried over sodium sulfate, filtered and concentrated in vacuo. The residue was purified by flash column chromatography (100 mL silica gel, 5:95 methanol-methylene chloride) to afford the desired product as a substantially pure white solid (198.5 mg, 89%). Crystals were obtained from toluene.

M.p.: 130 EC (dec.); R$_f$ 0.11 (5:95 methanol-methylene chloride); $^1$H NMR (400 MHz, Acetone-d$_6$) δ (mixture of carbamate rotamers) 8.34 (br s, 1H), 8.32 (br s, 1H), 6.31 (d, J=4.4 Hz, 1H), 6.14 (m, 1H), 5.97 (s, 1H), 5.97–5.90 (m, 1H), 5.90 (s, 1H), 5.68 (m, 1H), 5.42–5.37 (m, 2H), 5.31–5.22 (m, 2H), 5.18–5.1 (m, 1H), 4.85 (d, J=6.6 Hz, 1H), 4.65–4.55 (m, 2H), 4.38–4.34 (m, 1H), 4.26-4.22 (m, 1H), 3.89–3.86 (m, 1H), 3.77 (s, 3H), 3.71 (m, 1H), 3.57 (d, J=15.0 Hz, 1H), 3.48–3.43 (m, 1H), 3.25–3.13 (m, 2H), 3.00 (d, J=16.8 Hz, 1H), 2.34 (m, 1H), 2.11 (s, 3H); 13C NMR (101 MHz, Acetone-$d_6$) δ (mixture of carbamate rotamers) 169.4, 169.2, 153.8, 153.7, 150.6, 149.3, 148.2, 148.0, 145.5, 141.0, 135.1, 134.5, 133.9, 130.2, 130.1, 122.4, 117.9, 117.8, 117.7, 117.5, 114.2, 112.7, 111.0, 110.8, 108.4, 108.3, 102.1, 75.4, 66.74, 66.69, 65.6, 61.6, 61.2, 60.9, 54.3, 53.5, 52.9, 50.1, 49.3, 34.1, 33.6, 27.5, 9.7; FTIR (KBr) 3400 (s br), 2944 (m), 2881 (m), 1700 (s), 1639 (s), 1501 (w), 1463 (s), 1435 (s), 1356 (m), 1320 (m), 1288 (m), 1269 (m), 1238 (m), 1213 (m), 1166 (m), 1102 (s), 1065 (s), 1030 (m), 999 (m), 938 (m), 807 (w) cm$^{-1}$; HRMS (ESI), [m+H]/z calc=d for $C_{30}H_{33}O_{10}N_2$: 581.2135, found 581.2112; $[α]_D^{25}$ –27.2E (c0.50, methanol).

Example 6

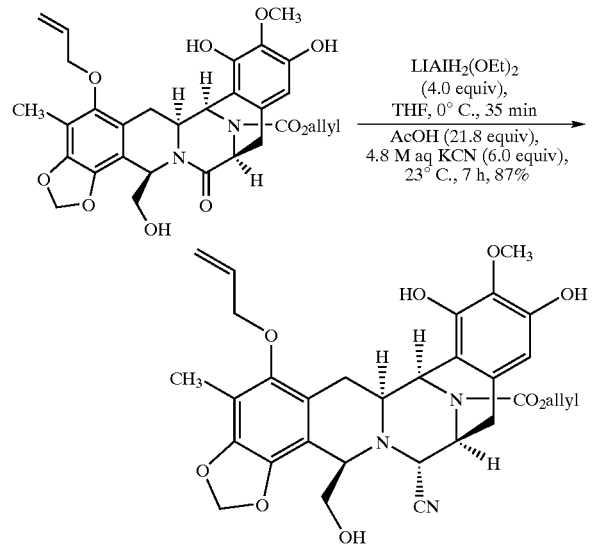

The amide (198.0 mg, 0.341 mmol) was dried by in vacuo azeotropic concentration with toluene (10 mL), dissolved in THF (10 mL) and cooled to 0 EC. A 0.20 M solution of LiAlH$_2$(OEt)$_2$ (6.8 mL, 1.36 mmol)[13] was added drop-wise over 10 min. The reaction was stirred at 0 EC for 35 min at afford the carbinolamine, $R_f$ 0.59 (4:1 ethyl acetate-hexane). Acetic acid (425 μL, 7.44 mmol) was added first in order to quench the reaction. Then 4.8 M aqueous potassium cyanide (425 μL, 2.04 mmol), anhydrous sodium sulfate (2.5 g, 17.6 mmol) and Celite[7] (6 mL) were added to affect the conversion to the amino-nitrile and to precipitate the aluminum salts. Bubbling was observed and after 5 min the reaction was warmed to 23 EC and stirred for 7 h. The suspension was filtered through a pad of Celite[7], eluting with ethyl acetate (100 mL). This solution was concentrated in vacuo and purified by flash column chromatography (100 mL silica gel, 2:1 ethyl acetate-hexane) to afford the desired product as a substantially pure white foam (175.6 mg, 87%).

$R_f$ 0.31 (4:1 ethyl acetate-hexane); $^1$H NMR (400 MHz, CDCl$_3$) δ (mixture of carbamate rotamers) 6.43 (br s, 0.6H), 6.26 (s, 0.4H), 6.24 (s, 0.6H), 6.20 (s, 0.4H), 6.07–6.00 (m, 1H), 5.97–5.82 (m, 4H), 5.61 (s, 0.6H), 5.52 (s, 0.4H), 5.37–5.17 (m, 3H), 4.90 (d, J=7.8 Hz, 0.4H), 4.84 (d, J=8.3 Hz, 0.6H), 4.73–4.60 (m, 2H), 4.16–4.08 (m, 2.6H), 3.97–3.94 (m, 1.4H), 3.77 (s, 1.2H), 3.68–3.61 (m, 3.62 (s, 1.8H), 3.49–3.36 (m, 1H), 3.29–3.19 (m, 3H), 2.76–2.69 (m, 1H), 2.11 (s, 1.8H), 2.08 (s, 1.2H), 2.00–1.83 (m, 2H); $^{13}$C NMR (101 MHz, CDCl$_3$) δ (mixture of carbamate rotamers) 154.3, 153.8, 148.4, 148.34, 148.26, 146.2, 145.9, 144.3, 138.8, 133.62, 133.56, 132.7, 132.2, 130.7, 130.3, 120.5, 120.3, 117.9, 117.8, 117.4, 117.2, 116.3, 112.6, 112.5, 112.1, 111.9, 107.2, 106.4, 101.1, 74.5, 74.0, 66.7, 66.5, 64.5, 64.3, 60.8, 60.5, 59.1, 58.9, 58.0, 56.7, 56.6, 49.9, 49.4, 48.9, 48.7, 31.2, 30.5, 29.7, 25.9, 9.43, 9.35; FTIR (neat) 3369 (m br), 2931 (m br), 1688 (m), 1500 (w), 1463 (m) 1431 (s), 1375 (m), 1325 (m), 1294 (m), 1269 (m), 1106 (s), 1063 (m), 994 (m), 956 (w) cm$^{-1}$; HRMS (ESI), [m+H]/z calc=d for $C_{31}H_{34}O_9N_3$: 592.2295, found 592.2316; $[α]_D^{25}$+30.4E (c 1.0, chloroform).

Example 7

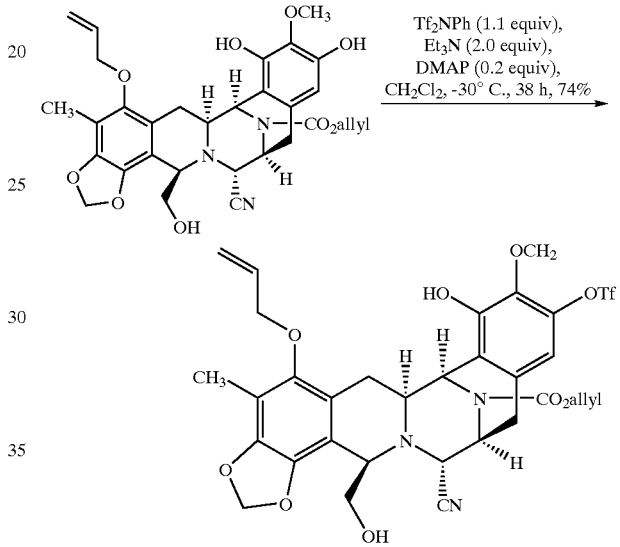

The phenol (170.0 mg, 0.287 mmol) was dried by in vacuo azeotropic concentration with toluene (10 mL) and dissolved in methylene chloride (3.0 mL). Triethylamine (80 μL, 0.574 mmol) and 4-dimethylaminopyridine (7.0 mg, 0.0574 mmol) were added and the solution was cooled to −30 EC in a dry ice-acetonitrile bath. N-Phenyltrifluoromethanesulfonimide (113.5 mg, 0.318 mmol) was added as a solid and the reaction was stirred at B30 EC in a Cryobath[7] for 38 h. The mixture was poured into 1:1 saturated aqueous sodium bicarbonate-saturated aqueous sodium chloride (100 mL), extracted with methylene chloride (2×75 mL), dried over sodium sulfate, filtered and concentrated in vacuo. The residue was purified by flash column chromatography (100 mL silica gel, gradient 2:3 to 3:4 ethyl acetate-hexane) to afford the desired product as a substantially pure clear film (153.4 mg, 74%).

$R_f$ 0.18 (2:3 ethyl acetate-hexane); $^1$H NMR (400 MHz, CDCl$_3$) δ (mixture of carbamate rotamers) 7.16 (s, 0.6H), 6.63 (s, 0.4H), 6.60 (s, 0.6H), 6.45 (s, 0.4H), 6.08–5.86 (m, 4H), 5.74 (m, 0.6H), 5.59 (m, 0.4H), 5.40–5.16 (m, 4H), 4.96-4.89 (m, 1H), 4.74–4.60 (m, 3H), 4.26 (m, 1H), 4.19–4.15 (m, 2H), 4.00 (m, 1H), 3.89 (s, 1.2H), 3.83 (s, 1.8H), 3.66–3.64 (m, 1H), 3.39–3.24 (m, 4H), 2.91–2.83 (m 2.11 (s, 1.2H), 2.05 (s, 1.8H), 1.86–1.78 (m, 1H); $^{13}$C NMR (101 MHz, CDCl$_3$) δ (mixture of carbamate rotamers) 154.0, 153.9, 148.6, 148.4, 147.3, 146.6, 144.7, 144.5, 141.3, 141.0, 139.1, 138.9, 136.9, 136.7, 133.7, 132.2, 132.1, 131.6, 129.4, 127.0, 123.0, 121.5, 121.3, 119.9, 118.5 (q, J=321 Hz, CF$_3$), 118.2, 117.7, 117.6, 117.4, 116.3, 116.1, 112.6, 112.3, 112.1, 112.0, 101.3, 101.2, 74.5, 66.9, 66.7, 65.7, 65.5, 62.0, 61.9, 59.54, 59.48, 58.6, 56.5, 49.8, 49.3, 49.0, 48.4, 31.0, 30.4, 26.1, 26.0, 9.5, 9.4; $^{19}$F NMR (376 MHz, BF$_3$$OEt$_2$ standard set at B153.0 ppm, CDCl$_3$) δ (mixture of carbamate rotamers) B74.02, −74.01; FTIR (neat) 3325 (w br), 2949 (w br), 1688 (m), 1588 (w), 1500 (m), 1425 (s), 1319 (m), 1288 (m), 1256 (m), 1213 (s), 1138 (s), 1106 (m), 1038 (m), 988 (m), 875 (w) cm$^{-1}$; HRMS (ESI), [m+H]/z calc=d for C$_{32}$H$_{33}$O$_{11}$N$_3$SF$_3$: 724.1788, found 724.1803; [α]$_D$$^{26}$+34.3E (c 1.0, chloroform).

Footnotes:

The following publications provide background information and are hereby incorporated herein by reference.

(1) The pioneering research in this area is due to Prof. Kenneth L. Rinehart and his group. See, (a) Rinehart, K. L.; Shield, L. S. in *Topics in Pharmaceutical Sciences*, eds. Breimer, D. D.; Crommelin, D. J. A.; Midha, K. K. (Amsterdam Medical Press, Noordwijk, The Netherlands), 1989, pp. 613. (b) Rinehart, K. L.; Holt, T. G.; Fregeau, N. L.; Keifer, P. A.; Wilson, G. R.; Perun, T. J., Jr.; Sakai, R.; Thompson, A. G.; Stroh, J. G.; Shield, L. S.; Seigler, D. S.; Li, L. H.; Martin, D. G.; Grimmelikhuijzen, C. J. P.; Gäde, G. *J. Nat. Prod.* 1990, 53, 771. (c) Rinehart, K. L.; Sakai, R; Holt, T. G.; Fregeau, N. L.; Perun, T. J., Jr.; Seigler, D. S.; Wilson, G. R.; Shield, L. S. *Pure Appl. Chem.* 1990, 62, 1277. (d) Rinehart, K. L.; Holt, T. G.; Fregeau, N. L.; Stroh, J. G.; Keifer, P. A.; Sun, F.; Li, L. H.; Martin, D. G. *J. Org. Chem.* 1990, 55, 4512. (e) Wright, A. E.; Forleo, D. A.; Gunawardana, G. P.; Gunasekera, S. P.; Koehn, F. E.; McConnell, O. J. *J. Org. Chem.* 1990, 55, 4508. (f) Sakai, R.; Rinehart, K. L.; Guan, Y.; Wang, H. J. *Proc. Natl. Acad. Sci. USA* 1992, 89, 11456.

(2) (a) *Business Week*, Sep. 13, 1999, p. 22. (b) *Science* 1994, 266, 1324.

(3) Corey, E. J.; Gin, D. Y.; Kania, R. *J. Am. Chem. Soc.* 1996, 118, 9202.

(4) Martinez, E. J.; Owa, T.; Schreiber, S. L.; Corey, E. J. *Proc. Natl. Acad. Sci. USA* 1999, 96, 3496.

(5) See Myers, A. G.; Kung, D. W. *J. Am. Chem. Soc.* 1999, 121, 10828 for a different approach to the synthesis of structures such as 5.

(6) For carboxylic acidBamine coupling methodology using CIP, see: (a) Akaji, K.; Kuriyama, N.; Kimura, T.; Fujiwara, Y.; Kiso, Y. *Tetrahedron Lett.* 1992, 33, 3177. (b) Akaji, K.; Kuriyama, N.; Kiso, Y. *Tetrahedron Lett.* 1994, 35, 3315. (c) Akaji, K.; Kuriyama, N.; Kiso, Y. *J. Org. Chem.* 1996, 61, 3350.

(7) The reagent LiAlH$_2$(OEt)$_2$ was prepared by the addition of a 1.0 M solution of LiAlH$_4$ in ether to a solution of 1 equiv of ethyl acetate at 0 EC and stirring at 0 EC for 2 h just before use; see: Brown, H. C.; Tsukamoto, A. *J. Am. Chem. Soc.* 1964, 86, 1089.

(8) For general reviews on reduction of lactones see: (a) Brown, H. C.; Krishnamurthy, S. *Tetrahedron*, 1979, 35, 567. (b) Cha, J. S. *Org. Prep. Proc. Int,* 1989, 21(4), 451. (c) Seyden-Penne, J. *Reduction by the Alumino- and Borohydrides in Organic Synthesis;* 2nd Ed.; Wiley-VCH: New York, 1997; Section 3.2.5.

(9) For general references on amide reduction by hydride reagents see ref. 7 and also Myers, A. G.; Yang, B. H.; Chen, H.; Gleason, J. L. *J. Am. Chem. Soc.* 1994, 116, 9361.

(10) Made from nitrogen purged water.

(11) This reagent was made by adding a 1.0 M solution of lithium aluminum hydride in Et$_2$O (1 equiv) to a solution of ethyl acetate (1 equiv) in Et$_2$O at 0 EC. The mixture was stirred at 0 EC for 2 h and a portion of this reagent was used for the reduction of the lactol. Brown, H. C.; Tsukamoto, A. *J. Am. Chem. Soc.* 1964, 86, 1089.

(12) Made from nitrogen purged water.

(13) See the reference cited in footnote 11.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. The process of Scheme 1, comprising the steps of:

(a) combining the compound 3b:

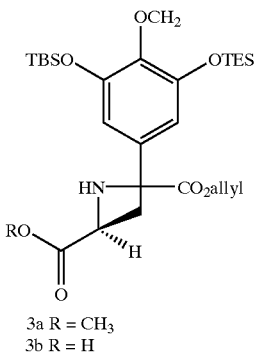

3a R = CH$_3$
3b R = H with the amino lactone 4:

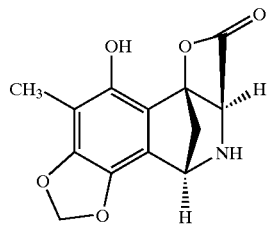

4 in the presence of an acylating reagent to form the coupled product 6:

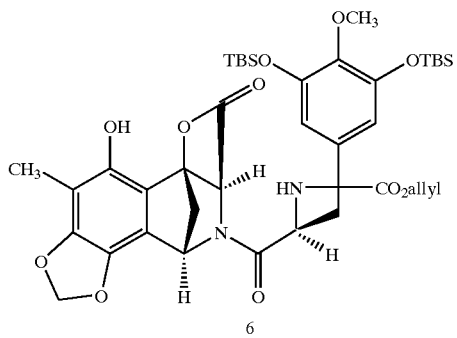

6

(b) treating compound 6 with an allyl bromide to give amide 7:

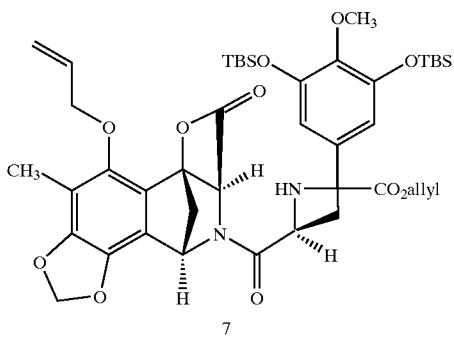

(c) reduction of the lactone compound 7 to the corresponding lactol, compound 8:

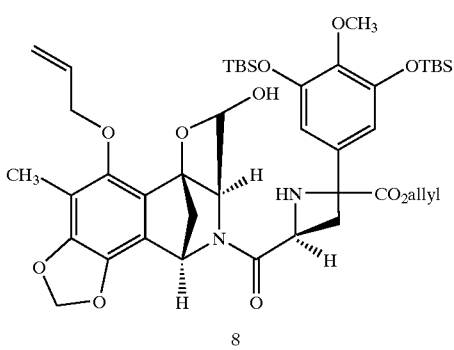

(d) desilylation of compound 8 to compound 9:

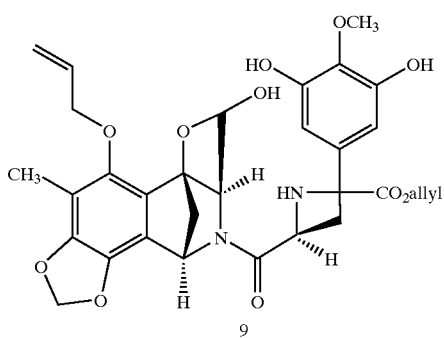

(e) cyclization of compound 9 to compound 10:

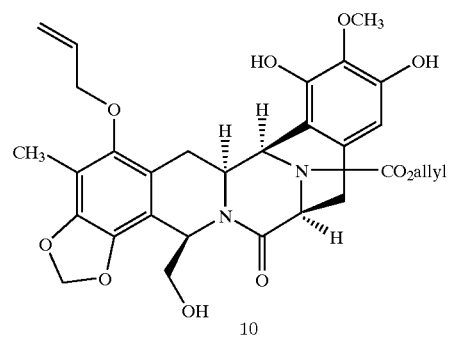

(f) reduction of the lactam in compound 10 to the corresponding cyclic aminal which upon exposure to HCN provided the pentacyclic amino nitrile, compound 5:

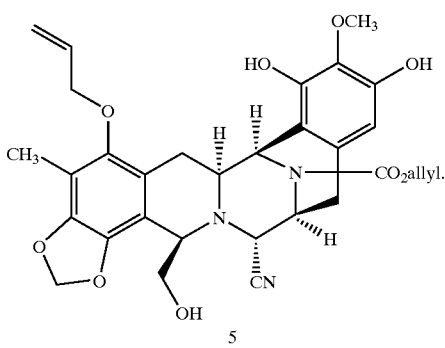

2. The process of Scheme 2, comprising the steps of:

(a) conversion of the compound 11:

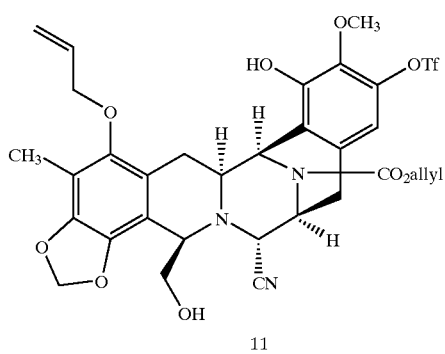

to the mono L-butyldimethylsilyl (TBS) ether, compound 12:

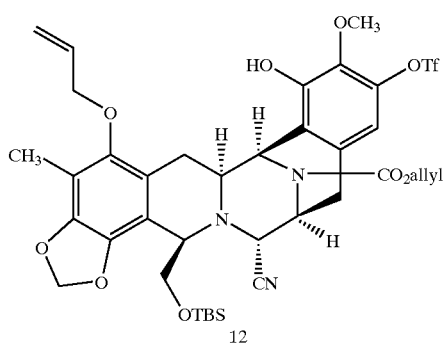

(b) etherification with methoxymethyl chloride to yield compound 13:

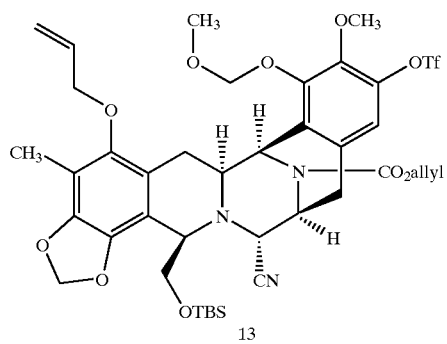

13

(c) cleaving the N-allyloxycarbonyl and O-allyl groups in 13 gives the secondary amine, compound 14:

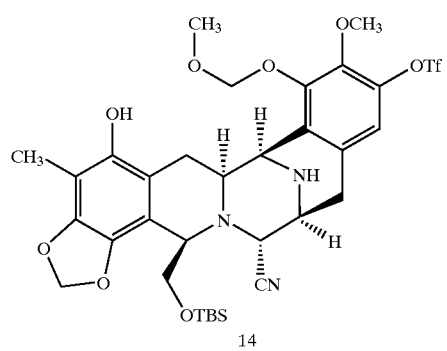

14

(d) N-methylation of compound 14 affords compound 15:

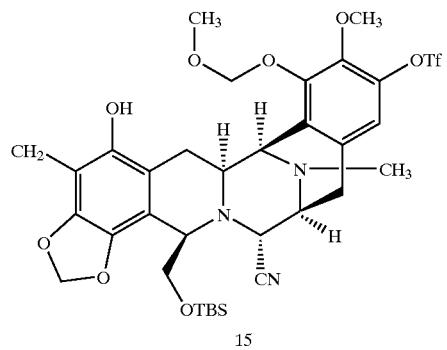

15

(e) C-methylation of compound 15 affords compound 16:

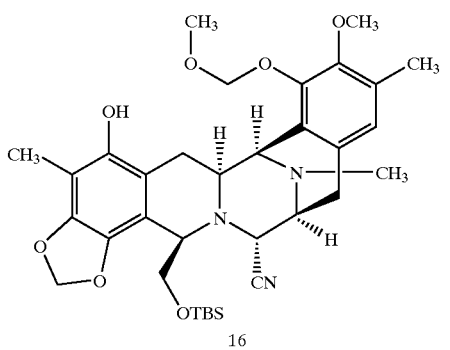

16

(f) acetylation of phenol 16 affords the corresponding acetate, compound 17:

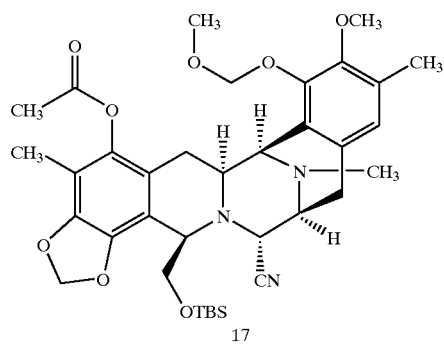

17

(g) desilylation of compound 17 yields the primary alcohol, compound 18:

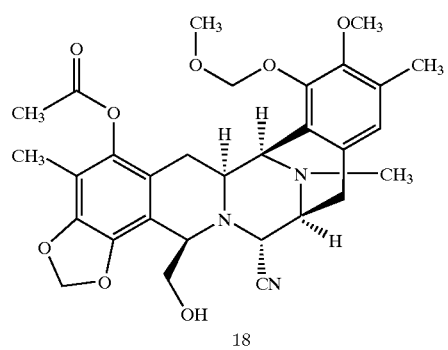

18

(h) Mitsunobu displacement of the primary hydroxyl of 18, yields the phthalimide, compound 19:

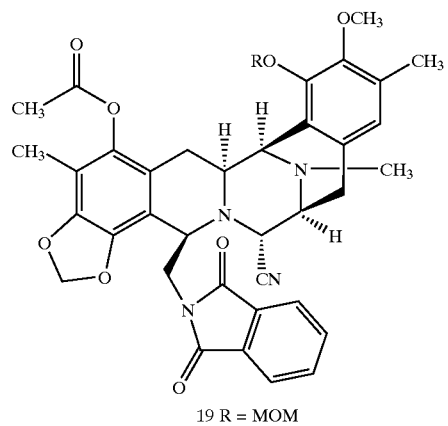

19 R = MOM (i) acid-catalyzed cleavage of the methoxymethyl ether in compound 19, generates compound 2-phthalascidin:

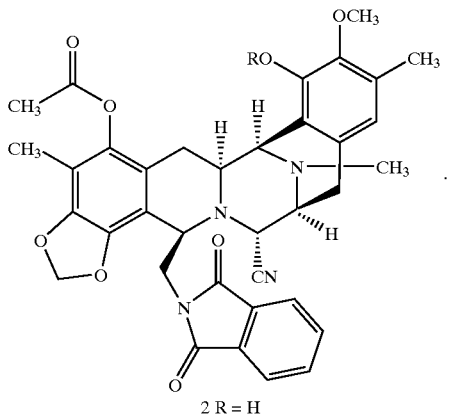

2 R = H

3. The synthetic intermediate of Scheme 1-compound 6:

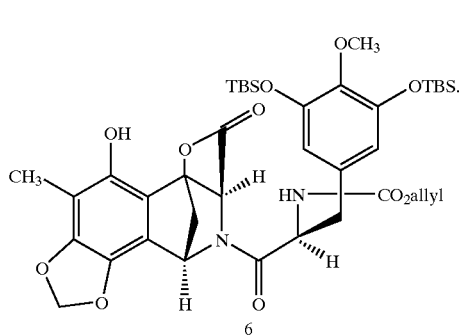

4. The synthetic intermediate of Scheme 1-compound 7:

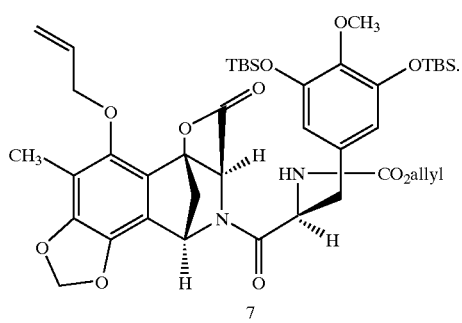

5. The synthetic intermediate of Scheme 1-compound 8:

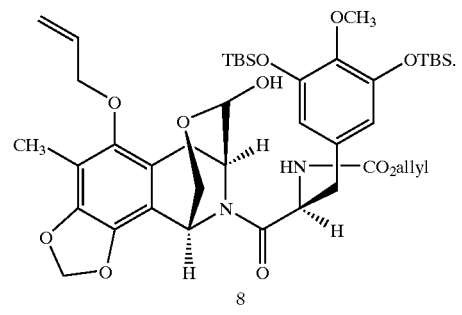

6. The synthetic intermediate of Scheme 1-compound 9:

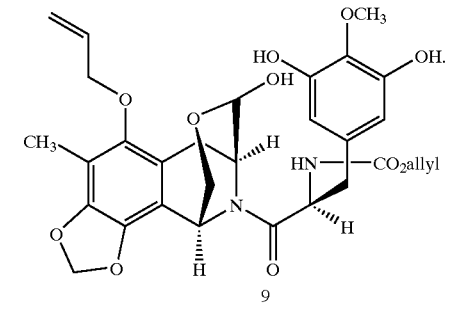

7. The synthetic intermediate of Scheme 1-compound 10:

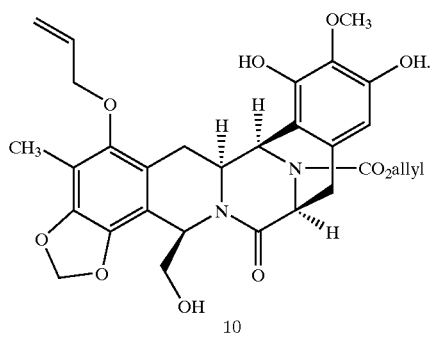

8. The synthetic intermediate of Scheme 2-compound 12:

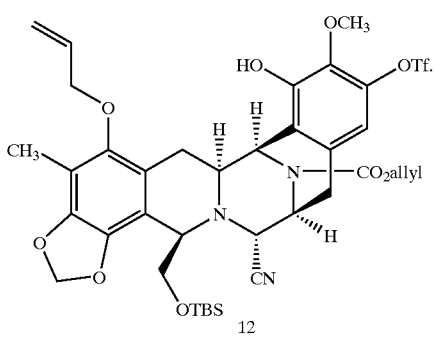

9. The synthetic intermediate of Scheme 2-compound 13:

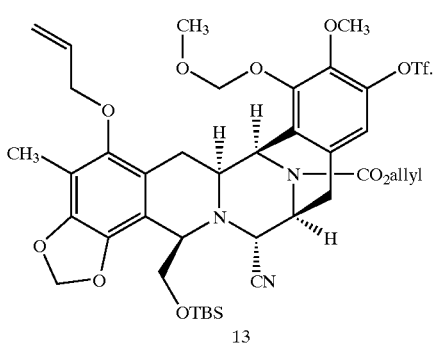

10. The synthetic intermediate of Scheme 2-compound 14:

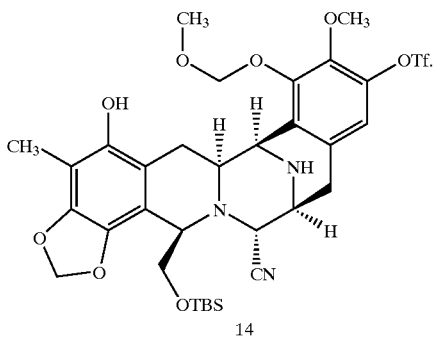

11. The synthetic intermediate of Scheme 2-compound 15:
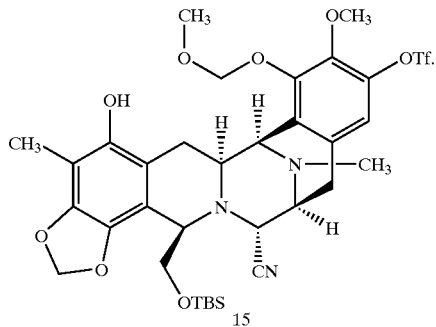
12. The synthetic intermediate of Scheme 2-compound 16:
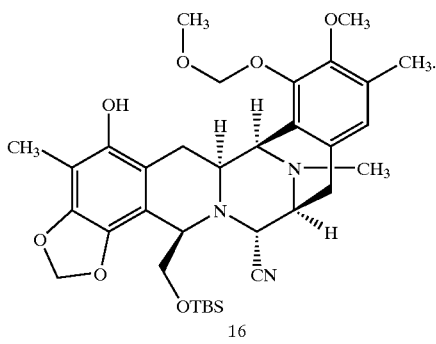
13. The synthetic intermediate of Scheme 2-compound 17:
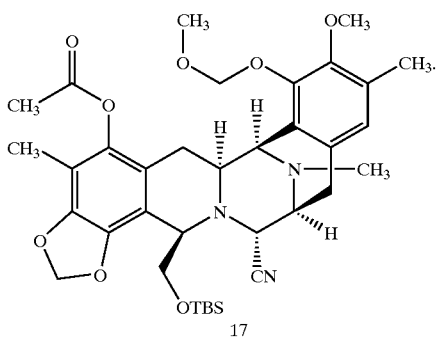
14. The synthetic intermediate of Scheme 2-compound 18:
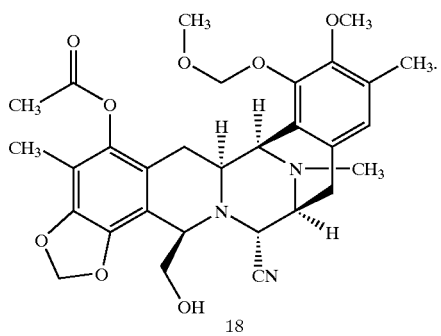
15. The synthetic intermediate of Scheme 2-compound 19:
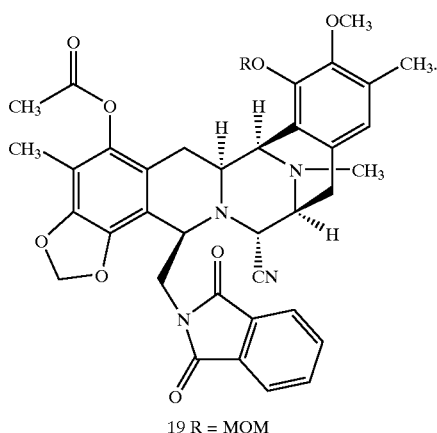
19 R = MOM
* * * * *

UNITED STATES PATENT AND TRADEMARK OFFICE
CERTIFICATE OF CORRECTION

PATENT NO. : 6,815,544 B2
APPLICATION NO. : 10/213711
DATED : November 9, 2004
INVENTOR(S) : Elias J. Corey It is certified that error appears in the above-identified patent and that said Letters Patent is hereby corrected as shown below:

In the abstract, at column 2, line 5, in Scheme 1 at column 3, and in claim 1 at column 16, line 38, kindly replace compound 4

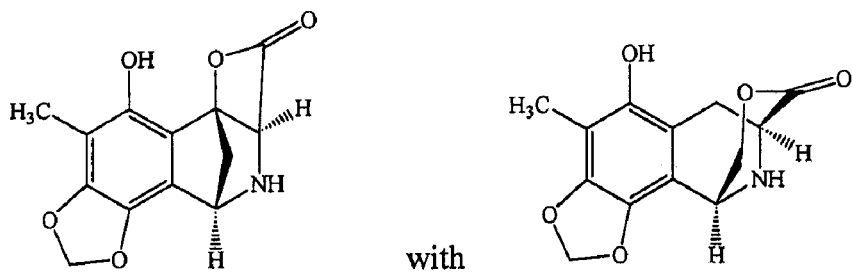

with

In Scheme 1 at column 4, kindly replace compound 5

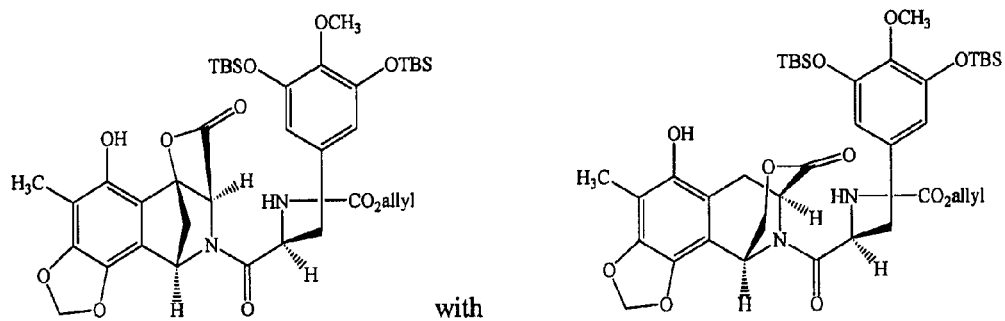

with

UNITED STATES PATENT AND TRADEMARK OFFICE
CERTIFICATE OF CORRECTION

PATENT NO.       : 6,815,544 B2
APPLICATION NO.  : 10/213711
DATED            : November 9, 2004
INVENTOR(S)      : Elias J. Corey It is certified that error appears in the above-identified patent and that said Letters Patent is hereby corrected as shown below:

In Scheme 1 at column 4, in claim 1 at column 17, line 3, and in claim 4 at column 21, line 21, kindly replace compound 7

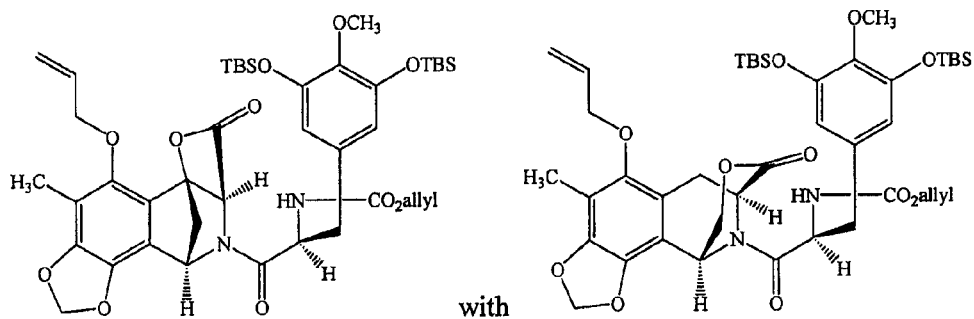

with

In Scheme 1 at column 3, and in claim 1 at column 17, line 20, kindly replace compound 8

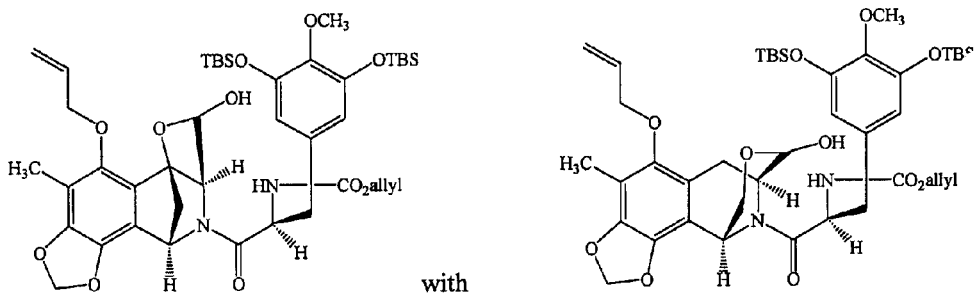

with

UNITED STATES PATENT AND TRADEMARK OFFICE
CERTIFICATE OF CORRECTION

PATENT NO.        : 6,815,544 B2
APPLICATION NO.   : 10/213711
DATED             : November 9, 2004
INVENTOR(S)       : Elias J. Corey It is certified that error appears in the above-identified patent and that said Letters Patent is hereby corrected as shown below:

In Scheme 1 at column 3, and in claim 1 at column 17, line 37, kindly replace compound 9

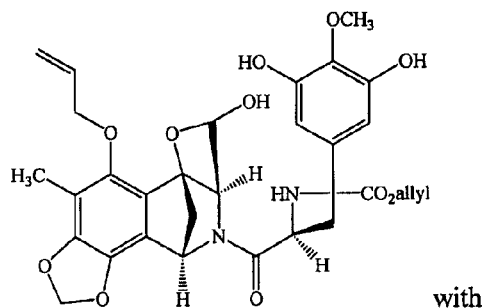 with 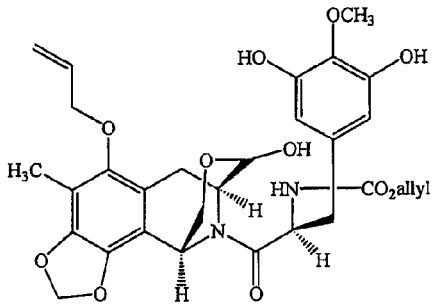

In Example 2 at column 9, line 13, kindly replace the compound

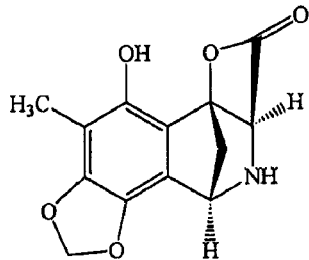 with 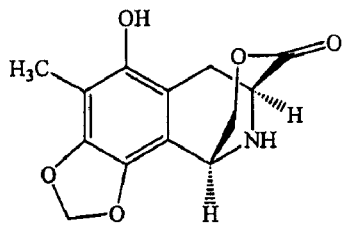

UNITED STATES PATENT AND TRADEMARK OFFICE
CERTIFICATE OF CORRECTION

PATENT NO. : 6,815,544 B2
APPLICATION NO. : 10/213711
DATED : November 9, 2004
INVENTOR(S) : Elias J. Corey It is certified that error appears in the above-identified patent and that said Letters Patent is hereby corrected as shown below:

In Example 2 at column 9, line 20, and Example 3 at column 10, line 20, kindly replace the compound

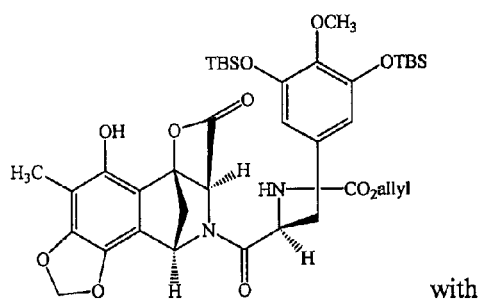 with 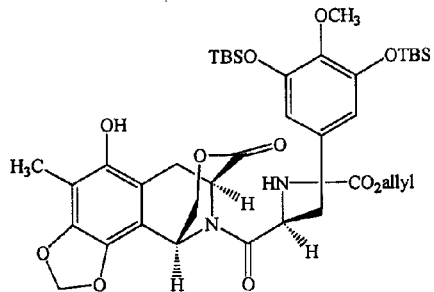

In Example 3 at column 10, line 33, and in Example 4 at column 11, line 20, kindly replace the compound

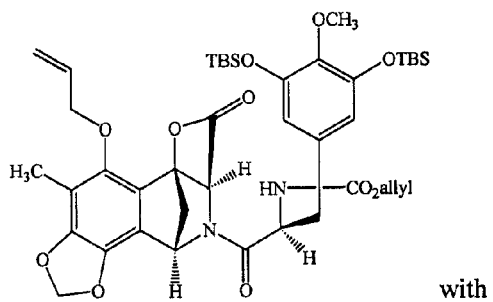 with 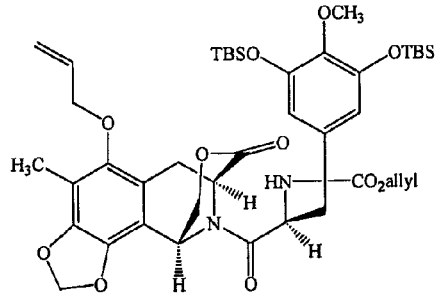

UNITED STATES PATENT AND TRADEMARK OFFICE
CERTIFICATE OF CORRECTION

PATENT NO. : 6,815,544 B2
APPLICATION NO. : 10/213711
DATED : November 9, 2004
INVENTOR(S) : Elias J. Corey It is certified that error appears in the above-identified patent and that said Letters Patent is hereby corrected as shown below:

In Example 4 at column 11, line 30, and in Example 5, column 12, line 18, kindly replace the compound

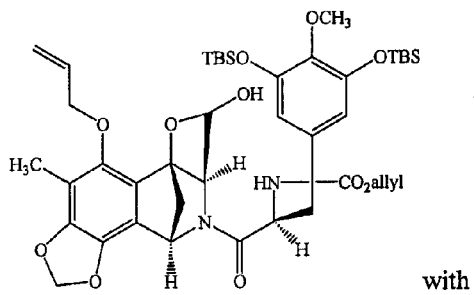 with 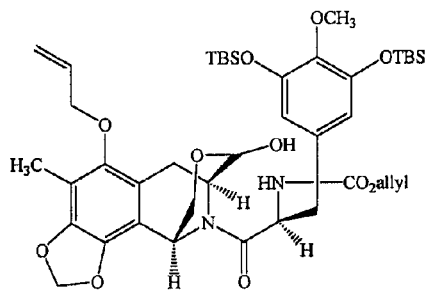

In claim 1 at column 16, line 53, and in claim 3 at column 21, line 4, kindly replace compound 6

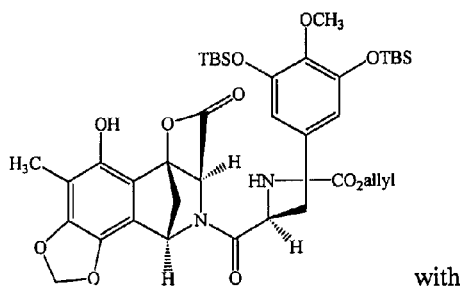 with 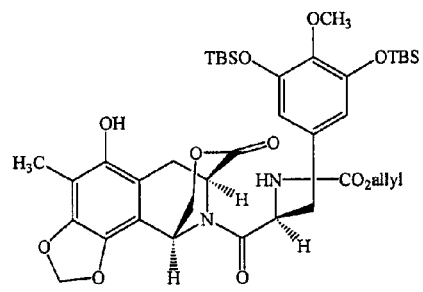

UNITED STATES PATENT AND TRADEMARK OFFICE
CERTIFICATE OF CORRECTION

PATENT NO.       : 6,815,544 B2
APPLICATION NO.  : 10/213711
DATED            : November 9, 2004
INVENTOR(S)      : Elias J. Corey It is certified that error appears in the above-identified patent and that said Letters Patent is hereby corrected as shown below:

In claim 5 at column 21, line 38, kindly replace compound 8

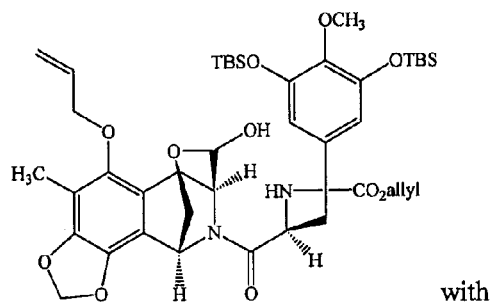 with 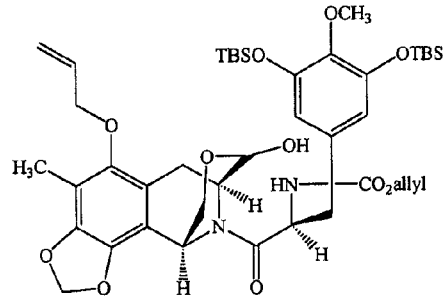

In claim 6 at column 21, line 54, kindly replace compound 9

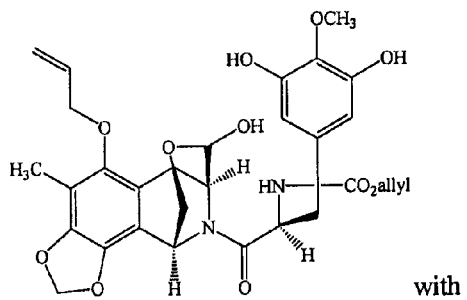 with 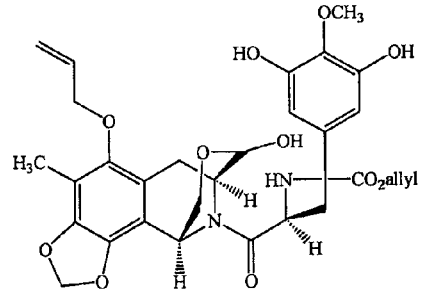

Signed and Sealed this

Twelfth Day of February, 2008

JON W. DUDAS
*Director of the United States Patent and Trademark Office*